（12）United States Patent
Barthel

(10) Patent No.: US 6,953,431 B2
(45) Date of Patent: Oct. 11, 2005

(54) ECCENTRIC DILATION BALLOONS FOR USE WITH ENDOSCOPES

(75) Inventor: James S. Barthel, Tampa, FL (US)

(73) Assignee: University of South Florida, Tampa, FL (US)

( * ) Notice: Subject to any disclaimer, the term of this patent is extended or adjusted under 35 U.S.C. 154(b) by 125 days.

(21) Appl. No.: 10/408,831

(22) Filed: Apr. 4, 2003

(65) Prior Publication Data

US 2004/0015052 A1 Jan. 22, 2004

Related U.S. Application Data

(60) Provisional application No. 60/371,754, filed on Apr. 11, 2002.

(51) Int. Cl.⁷ .................................................. A61B 1/04
(52) U.S. Cl. .......................... 600/116; 600/104; 600/115
(58) Field of Search ........................ 604/96.01; 600/104, 600/106, 114–116; 121, 153

(56) References Cited

U.S. PATENT DOCUMENTS

| | | |
|---|---|---|
| 4,083,369 A | 4/1978 | Sinnreich |
| 4,862,874 A | 9/1989 | Paulson et al. |
| 5,030,227 A | 7/1991 | Rosenbluth et al. |
| 5,103,804 A | 4/1992 | Abele et al. |
| 5,271,383 A | 12/1993 | Wilk |
| 5,312,430 A | 5/1994 | Rosenbluth et al. |
| 5,314,443 A | 5/1994 | Rudnick |
| 5,331,947 A | 7/1994 | Shturman |
| 5,409,483 A | 4/1995 | Campbell et al. |
| 5,645,529 A | 7/1997 | Fagan et al. |
| 5,662,608 A | 9/1997 | Imran et al. |
| 5,667,493 A | 9/1997 | Janacek |
| 5,669,880 A | 9/1997 | Solar |
| 5,718,680 A | 2/1998 | Solar |
| 5,807,331 A | 9/1998 | den Heijer et al. |
| 5,827,175 A * | 10/1998 | Tanaka ...................... 600/104 |
| RE36,104 E | 2/1999 | Solar |
| 5,882,336 A | 3/1999 | Janacek |
| 5,899,882 A | 5/1999 | Waksman et al. |
| 5,980,484 A | 11/1999 | Ressemann et al. |
| 6,306,074 B1 | 10/2001 | Waksman et al. |
| 6,488,653 B1 | 12/2002 | Lombardo |
| 6,508,784 B1 | 1/2003 | Shu |
| 2001/0049497 A1 | 12/2001 | Kalloo et al. |
| 2002/0072706 A1 | 6/2002 | Hiblar et al. |
| 2002/0087100 A1 * | 7/2002 | Onuki et al. ................ 600/585 |
| 2002/0193660 A1 | 12/2002 | Weber et al. |
| 2003/0045859 A1 | 3/2003 | Dominguez |

FOREIGN PATENT DOCUMENTS

| | | |
|---|---|---|
| EP | 0 345 051 | 12/1989 |
| FR | 2 738 489 | 3/1997 |
| JP | 1015063 | 1/1989 |

OTHER PUBLICATIONS

Saab, M. A. "Applications of High–Pressured Ballons in the Medical Device Industry", 1999, Advanced Polymers, Inc.

* cited by examiner

Primary Examiner—Beverly M. Flanagan
(74) Attorney, Agent, or Firm—Saliwanchik, Lloyd & Saliwanchik

(57) ABSTRACT

The dilation balloon of the subject invention preferably comprises a balloon portion mounted about a shaft that, when inflated, produces a configuration comprising a tapered distal end and a proximal end or butt that is substantially flat (preferably truncated) and is adapted to generally conform with the outer contours of an endoscope through which it is introduced when the balloon is pulled back against the endoscope face. The close engagement of the subject balloon catheter and endoscope, when forming a balloon-scope train, enables the scope to more readily navigate strictures and tortuous body lumen, as well as allows the balloon to act as a lens for viewing anatomical structure within the body lumen, such as tumors, strictures, and the inner luminal wall surface itself.

52 Claims, 4 Drawing Sheets

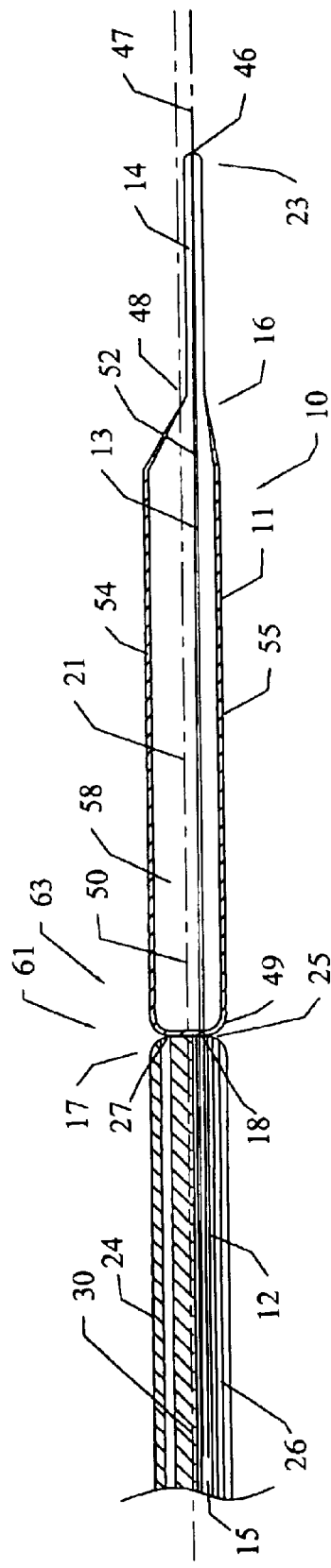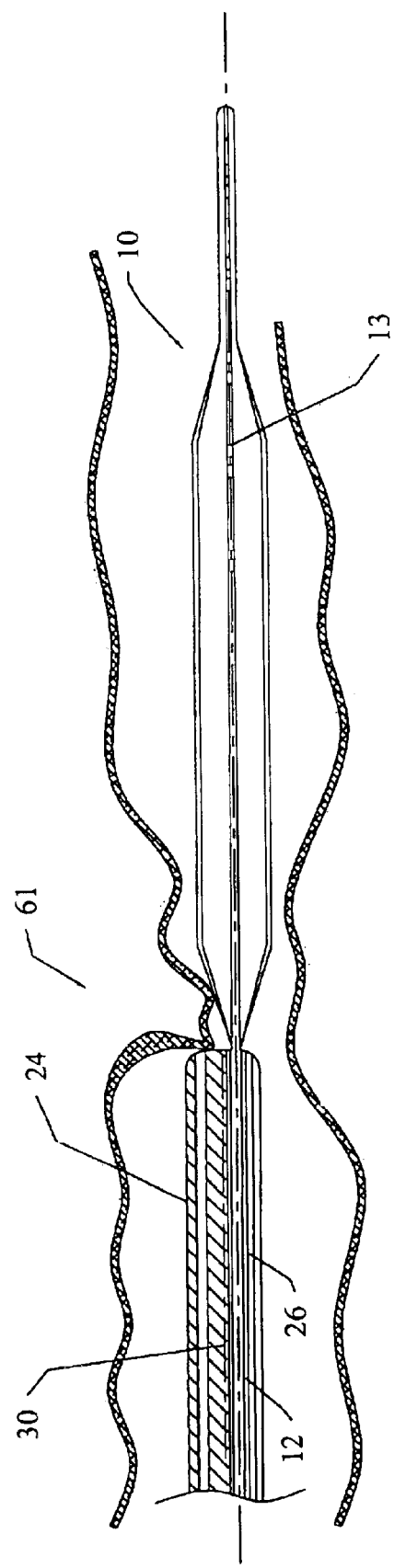

ECCENTRIC DILATION BALLOONS FOR USE WITH ENDOSCOPES

CROSS-REFERENCE TO RELATED APPLICATION(S)

This application claims the benefit of provisional patent application Ser. No. 60/371,754, filed Apr. 11, 2002, which is hereby incorporated by reference in its entirety, including all figures, tables, and drawings.

TECHNICAL FIELD

This invention relates to medical devices, more particularly to balloons used in endoscopy to dilate strictures.

BACKGROUND OF THE INVENTION

Through the endoscope, balloon dilation of tight esophageal strictures is frequently carried out with fluoroscopic monitoring. A stricture is considered to be "tight" if an endoscope cannot be passed through it. Fluoroscopic monitoring of tight stricture dilation is believed to help prevent sudden fracture or splitting of the stricture and thus reduce the risk of esophageal perforation during the dilation procedure. Currently available dilation balloons are made of transparent material. However, the tapered or domed butt design of the proximal end of currently available dilation balloons severely limits stricture wall visualization when the face of the endoscope is approximated to the butt of the balloon. Also, the misalignment produced by current dilation balloon design between the dilation balloon and endoscope insertion shaft as described below further limits stricture wall visualization. Therefore, fluoroscopic monitoring must be relied upon for monitoring purposes.

Examination and accurate measurement of an esophageal stricture can only be accomplished visually or endosonographically if the endoscope can be passed completely through the stricture. Two techniques exist for accomplishing complete stricture passage with balloon dilation. The traditional method is to pass and inflate successively larger balloons across the stricture until a diameter of 15 to 16 mm is achieved. The last dilation balloon is then removed and the instrument is maneuvered through the stricture under direct unguided operator control. The post-dilation 15 or 16 mm diameter stricture lumen is 5 or 6 mm larger than the diameter of a standard video endoscope and 2 to 3 mm larger than the diameter of an echoendoscope. However, stricture elasticity, luminal tortuosity, and frequent shelving (stepped areas along the stricture) can prevent passage of the instrument, despite an apparently adequate dilation.

An alternative method for accomplishing complete stricture passage with balloon dilation is the "balloon-scope train method". The stricture is dilated to a diameter 1 or 2 mm larger than the diameter of the endoscope. The endoscope is then pushed up against the proximal end of the inflated dilation balloon to form a balloon-scope "train". The combination of balloon and endoscope is then advanced through the stricture. Although currently available dilation balloons are made of transparent material, their design permits only limited monitoring and inspection of the stricture wall as the maneuver is carried out.

Unfortunately, current dilation balloon design hinders not only visualization of the stricture wall during dilation and subsequent instrument passage, but also actively impedes the passage of the "balloon-scope train". FIG. 1 depicts a currently available esophageal dilation balloon (for example, the QUANTUM TTC® Balloon Dilator, which is the subject of U.S. Pat. No. 5,681,344 to Kelly) and endoscope in a "balloon-scope train" configuration. Because the instrument accessory channel outlet on the endoscope face is off-center with respect to the endoscope insertion shaft and the balloon support wire is centered with respect to the balloon, the flat face of the endoscope protrudes over one side of the balloon. The protruding endoscope face tends to catch tumor shelves and resist passage through tortuous areas resulting in difficult passage and on occasion failure of passage. Also, because the current tapered or domed butt balloon designs prevent the endoscope from being cinched up tight against the rear of the balloon, a significant gap is created, which exacerbates the tendency of the endoscope face to catch on tumor shelves and in tortuous areas of a stricture.

What is needed is a dilation balloon that will permit direct visualization of the stricture wall through the transparent material of the balloon for purposes of stricture wall monitoring during dilation and that will align properly with the insertion shaft of the endoscope to facilitate passage of the endoscope through the stricture using the balloon-scope train method.

SUMMARY OF THE INVENTION

The dilation balloon of the subject invention preferably comprises a balloon portion mounted about a shaft that, when inflated, produces a configuration comprising a tapered distal end and a proximal end or butt that is substantially flat (preferably truncated) and is adapted to generally conform with the outer contours of the endoscope through which it is introduced when the balloon is pulled back against the endoscope face. The close engagement of the subject balloon catheter and endoscope, when forming a balloon-scope train, enables the scope to more readily navigate strictures and tortuous body lumen, as well as allows the balloon to act as a lens for viewing anatomical structure within the body lumen, such as tumors, strictures, and the inner luminal wall surface itself. The term "engage" is used herein to define when the balloon portion and endoscope come into contact in a manner made possible by the configuration of the balloon portion such that the scope and balloon portion generally fit closely against, or couple with one another, to generally form a single functional unit. Generally, the balloon portion is positioned relative to the shaft such that the central axis of the balloon portion and the central axis of the endoscope are generally in alignment with one another when in engagement, regardless of the position of the instrument channel along the endoscope face. As used herein, the term "endoscope" includes any elongate medical device having a viewing lens, port, camera, etc., located about the distal end thereof that is capable of remote transmission of images from within the body of a patient, through video, ultrasound and other energy waves, direct observation, etc. to a screen, viewing port, etc. where it can be viewed by a clinician, typically in real time.

In one embodiment of the present invention, the dilation balloon includes a shaft made of a flexible catheter tubing, such as Pellethane; a balloon portion made of non-compliant material, such as transparent polyethylene terephthalate (PTE); a support element, such as a solid, tapered nitinol wire that extends from the distal end of the shaft and longitudinally traverses the balloon; and a flexible tip portion. Unlike the standard PTE dilation balloon, the cross-sectional center of the present balloon is offset relative to both the balloon shaft, which supplies infustate to fill the balloon, and the support wire. This offset results in the balloon having an eccentric shape following inflation, relative to the luminal axis, which comprises the original passageway that extends longitudinally through the balloon portion, intersecting the distal and proximal openings. The degree of offset generally corresponds to the distance between the instrument or working channel of the endoscope and the scope's central axis, thus allowing the balloon, when inflated and properly oriented, to become concentrically aligned with the scope and generally eliminating or reducing exposure of the otherwise-protruding edge along the endoscope face. This allows the balloon-scope train, which generally forms a common cylindrical unit, to be navigated through a complex stricture with greater ease by better protecting the endoscope face from butting against a shelf or other portion of a stricture during advancement. As used herein, a "common cylindrical unit" is defined as endoscope and balloon catheter combination in which the inflated balloon portion, when fully abutted against the endoscope face, generally extends distally therefrom as a continuous unit and without any significant gaps existing between the proximal end of the balloon portion and the distal face of the endoscope. Furthermore, the balloon portion is generally concentrically aligned with the body of the scope. The balloon portion can be somewhat larger or smaller than the scope, or increase or decrease in diameter somewhat over its length; however, the balloon provides a functional extension that generally follows the contours of the scope for at least a portion of the balloon's length, such as up until the distal taper. With regard to the cross-sectional profile of the balloon, the definition of "cylindrical" would include a tubular shape that is not generally round. For example, the balloon portion may comprise an elongate, but squarish or triangular shape. Furthermore, it should be noted that the present invention does not necessarily require that all embodiments of the balloon portion form a common cylindrical unit with the endoscope. For example, the balloon portion may be spherical or some other shape, yet comprise a material or configuration that allows it to effectively abut and engage the endoscope face to function in the manner previously described.

In another aspect of the invention, the balloon is formed such that the proximal end is generally truncate in shape, having a substantially flat butt, rather than comprising a standard tapered or domed configuration. The truncated end permits all or a substantial portion of the endoscope face to be drawn up against the proximal end of the balloon, thereby significantly reducing or eliminating any gaps that would otherwise exist. By advancing the endoscope face and viewing port against the transparent balloon material, the liquid-filled balloon acts like a lens to permit improved visualization of the anatomical structures adjacent to the balloon. This is especially significant during a dilation procedure in the esophagus. With the goal of being able to achieve maximum dilation of the stricture or tumor without causing a fissure to form in the esophageal wall due to over-inflation of the balloon, being able to clearly visualize and monitor the tissues during inflation provides an important clinical benefit over existing treatment modalities, especially fluoroscopy, during which detection of a developing fissue is generally not possible. In addition, when filled with a liquid, such as water or saline, typically acts like a magnifying lens to make structures adjacent the walls of the balloon appear larger, thus aiding with diagnosis and monitoring of a procedure.

In yet another aspect of the present invention, the balloon catheter includes an inner shaft that extends from within the main shaft and through the balloon portion, instead of a support wire, to accommodate optional ancillary instrumentation that may be used in a procedure, such as a standard wire guide. The inner shaft terminates about the distal tip portion, which includes a passageway via which the wire guide may enter and exit the balloon catheter to aid in cannulation or perform some other function. The infustate for inflation of the balloon is supplied via the outer shaft through the space between the outer and inner shafts.

In still yet another aspect of the invention, the posterior end of the balloon portion is further modified to facilitate positive engagement with the face of the endoscope and/or aid with alignment between the endoscope and balloon when the endoscopist is drawing the balloon back against the scope. In one embodiment, the positive end of the balloon portion is concave in shape to receive the distal face of the endoscope, which typically has a rounded shape. In a different embodiment, the posterior end of the balloon portion includes a guide element, such as one or more rings, flaps, ridges, etc. affixed around the outer ridge of the posterior end that could guide and/or align the tip of the endoscope against the posterior end of the balloon portion. The guide element(s) may also serve to further shield any gap that exists between the scope and balloon to prevent tissue or materials from entering that space, possibly causing an obstruction that hinders further advancement or impairs visibility. A different approach to facilitating alignment between the balloon portion and endoscope is found in an embodiment that provides an alignment marking on the portion of the catheter external to the scope, such as the proximal hub. The marking is positioned such that when oriented in a predetermined manner, the larger side of the eccentric balloon is aligned with the corresponding side of the endoscope face, typically having the viewing port or lens, such that the scope and balloon are generally aligned concentrically.

All patents, patent applications, and publications referred to herein are incorporated by reference in their entirety to the extent they are not inconsistent with the explicit teachings herein.

BRIEF DESCRIPTION OF THE DRAWINGS

Embodiments of the present invention will now be described by way of example with reference to the accompanying drawings, in which:

FIG. 1 depicts a partially-sectioned side view of a prior art dilation balloon being used with a standard endoscope;

FIG. 2A depicts a partially-sectioned side view of the illustrative embodiment of the present invention in engagement with the endoscope of FIG. 1;

DETAILED DESCRIPTION OF THE DRAWING

Figure 2B:
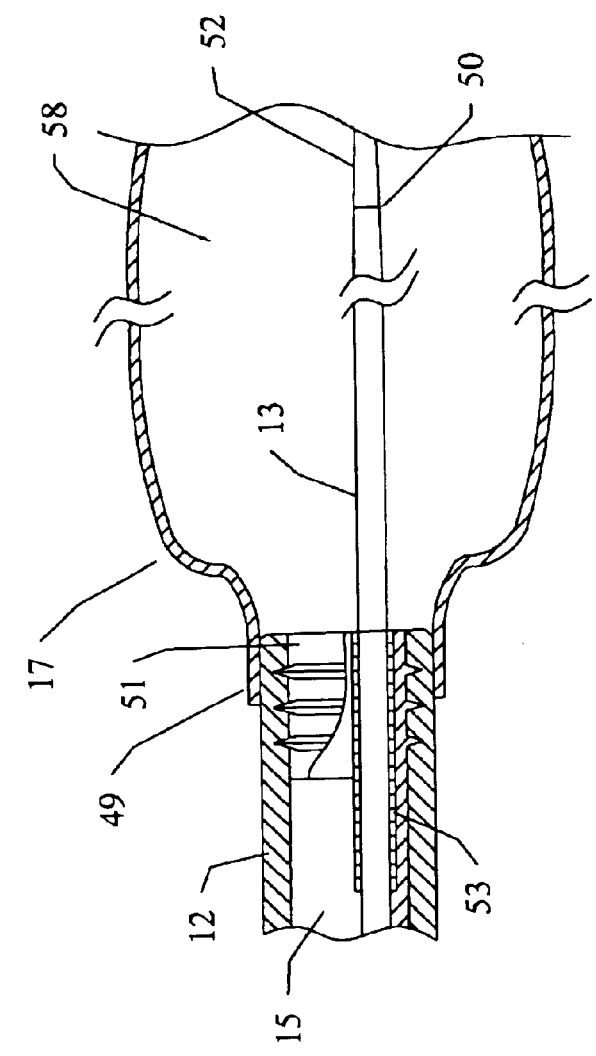
FIG. 2B depicts a partially-sectioned detail view of the embodiment of FIG. 2A.

The present invention includes embodiments of a balloon catheter 10, such as that depicted in FIG. 2, configured for engagement with an endoscope to facilitate negotiation of the scope through a stricture or other difficult or tortuous pathway within the body, and/or to abut the viewing port 27 or objective lens of the endoscope face such that anatomical structures of interest can be viewed. The illustrative balloon catheter 10 comprises a dilation balloon portion 11; typically made of a clear, non-distensible polymer material such as transparent polyethylene terephthalate (PET); a shaft, made of a flexible catheter material 12 attached proximally to the balloon portion and having a passageway 15 that communicates with the balloon portion 11 to supply infusate, such as water, or saline, to expand the balloon; a support element 13 or wire, that extends beyond the distal end 18 of the shaft, through the distal end 16 of the balloon, and terminating within a flexible tip portion 14, made of a suitable medical grade elastomer tubing, such as Pelethane 2363-80AE. The tip portion 14, which generally provides an atraumatic means of cannulating a stricture or generally guiding the balloon through a passageway, includes a rounded tip with the central bore of the tip 46 being filled with an adhesive at the distal end 16. In an embodiment of the subject invention, the support element 13 is a kink-resistant material such as nitinol, stainless steel, or other non-superelastic materials and alloys.

Figure 3:
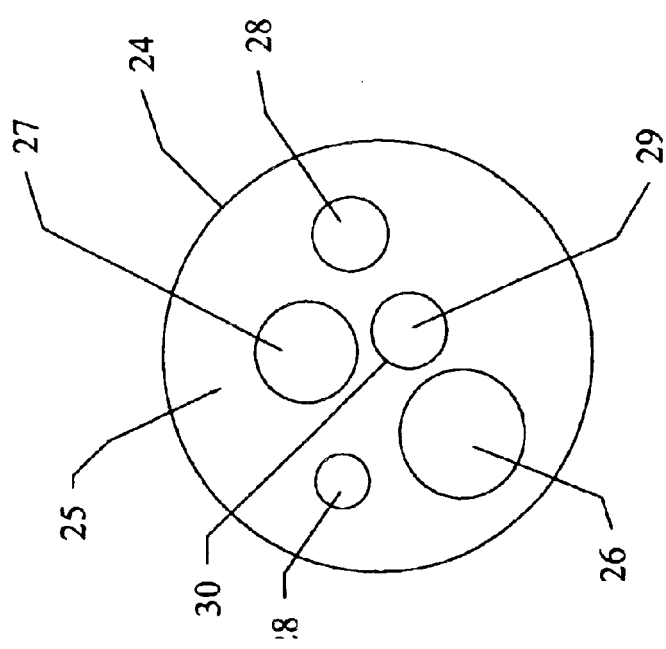
FIG. 3 depicts an end view of the face of a standard endoscope having an instrument channel offset from the central axis.

The illustrative balloon portion 11, depicted in FIGS. 2A–2B, comprises a main portion 57 that is generally uniformly cylindrical in shape, and a tapered portion 22 toward the distal end 16 of the balloon portion 11. The proximal end 17 of the balloon portion 11 is generally truncate in shape such that the proximal end 17 can be cinched or drawn against the distal face 25 of an endoscope 24 from which it has been advanced, such that there is broad area of contact between the balloon portion 11 and at least a substantial cross section of the endoscope face 25, which is depicted in FIG. 3. the area of contact includes the viewing port 27 or objective lens, and preferably, but not essentially, the light source 28 such that the balloon portion generally serves as an extension of the lens 27, thereby enabling the endoscopist a relatively unobstructed and undistorted view through the balloon interior 58, which permits visualization of the anatomical structures within the body conduit. When obstructions from tissues or fluids do occur, they still can be dislodged from the lens or space between the balloon and endoscope using a stream of saline, water, etc. delivered from the flush port 29. When illustrative balloon portion 11 is inflated and held against the endoscope 24, the resulting balloon-scope train 61 generally forms a common cylindrical unit 63.

The main portion 57 of the balloon portion 11 includes a central axis 21 that intersects the cross-sectional center point of the main cylindrical portion 57. The balloon portion 11 also includes a luminal axis 47 that intersects the proximal 49 and distal 48 openings 48, 49 of the balloon portion. The luminal axis 47 of the present invention comprises the original lumen of the tubing used to form the balloon portion 11, but unlike a standard dilation balloon, such as the '344 balloon, is offset relative to the central axis 21 to allow alignment with the endoscope. Generally, it is desired that the balloon portion 11 and outer contours of the endoscope 24 be concentrically aligned with one another to maximize the field of view and reduce ledges or surfaces that are prone to catch upon a shelf or stricture during advancement of the balloon-scope train 61. Although having the balloon diameter closely match that of the endoscope provides the ideal clinical situation for introduction of the balloon-scope train 61, it is not necessary to the invention that the balloon and scope be of the same diameter. Often, multiple sizes of balloons are used with a given endoscope for a single procedure, such as in esophageal dilation procedures, where attempting to filly dilate in a single, rather than multiple stages, increases the risk of rupture. The standard sizes of endoscopes used in gastrointestinal procedures are 8.5, 9.5, and 11.5 mm, which are generally compatible with the most preferred range of balloon diameters for the illustrative embodiment (10–16 mm).

The balloon portion 11 and shaft 12 are attached to one another by inserting the distal end 18 of the shaft 12 into the proximal opening 49 and bonding thereto using a well-known method such as an ultraviolet-curable adhesive. The shaft 12, which is aligned with the luminal axis 47, is therefore, offset relative to the central axis 21. Also aligned with the luminal axis 47, is the support element 13, or stiffener, which can be, but is not to be limited to, for example, a 0.027" solid flexible nitinol wire, that extends the length of the catheter shaft 12, through the balloon portion 11, then terminating within the tip portion 14. The support element 13 includes a tapered portion 52 that begins at a point 50 within the interior 58 of the balloon portion and tapers down about two-thirds the original diameter (in this example, approximately 0.010") at the tip 23. As shown in FIG. 2a, the support element 13 is attached to an insert 51 that is embedded into the sheath lumen 15 about the distal tip. The insert, is preferably, but not essentially, made of a physiologically inert, radiopaque material, such as 303 stainless steel. To avoid the difficulty of soldering to the support element 13, a piece of metal cannula 53 is crimped over the support wire 13 and soldered or otherwise affixed to the insert 51, thereby longitudinally securing the support wire relative to the shaft 12 and balloon portion 11.

In the illustrative embodiment, the catheter shaft 12 includes a single lumen 15 that houses the support element 13 and provides an infusion pathway to the balloon portion 11, whereby water or saline is introduced, via the hub, using a commonly-available infusion device appropriate for the balloon volume. The balloon is maintained in a deflated state and is folded and inserted into a delivery sheath (not shown). It is then advanced from the delivery sheath into the instrument (accessory) channel of the endoscope, which typically is a minimum of 2.8 mm for the illustrative esophageal dilation balloon, as well as the related pyloric, or colonic embodiments in which the balloon is 18 mm or smaller in diameter when inflated. Larger diameter balloons, e.g., 19–20 mm, may require an instrument channel of up 3.7 mm or greater. Typically, the balloon is lubricated to ease insertion into the endoscope instrument channel. The shaft 12 of the illustrative embodiment and related embodiments has an OD of approximately 0.085" and an ID of approximately 0.058". The esophageal and colonic embodiments typically have an overall length, including balloon, of approximately 180 cm, although any length that is appropriate for a particular endoscope may be used. The colonic dilation balloon catheter 10 is typically longer, e.g., 240 cm.

The balloon portion 10 of the illustrative embodiment of FIG. 2 is formed by a well-known means, such as blow molding, whereby a length of PTE tubing, sufficient in length to form the final desired length of the balloon, is placed and clamped within a mold conforming to the final shape of the fully distended balloon. Hot air is passed through the tubing, causing the tubing to expand against the contours of the mold. The tubing and molding process parameters necessary to achieve the desired balloon are determined by the required burst strength and recommended pressure of the balloon, the material used, and the size of the balloon. One source of the balloon portion 10 of the illustrative embodiment is Advanced Polymers, Inc. (Salem, N.H.). The typical range of diameters for an 8 cm long esophageal dilation balloon is generally about 6 to 19 mm, with a more preferred range of 12–18 mm. Minimum specified burst pressures typically average 175 psi for a 12 mm balloon, down to about 122 mm for an 18 mm diameter balloon, with the corresponding recommended pressures being about 90 and 50 psi, respectively. Pyloric and colonic dilation balloons are typically shorter in length (e.g., 5.5 cm); however, the recommended pressures are generally the same as the longer esophageal balloons for corresponding diameters. In the illustrative invention, the balloon portion 11, because of its eccentric shape, is divisible into a first longitudinal portion 54 and a second longitudinal portion 55 along the luminal axis 47, with the first longitudinal portion 54 comprising the larger volume of the two. Because the original tubing requires greater expansion within one side of the eccentric-shaped mold than the other to contact the outer mold surface, the thicknesses found along the wall 59 of the first longitudinal portion 54 will generally be thinner than that found along the wall 60 of the second longitudinal portion 55. Generally, the thickness and strength of the first portion wall 59 determines the burst and recommended pressures that are specified for a given balloon catheter 10.

Figure 4A:
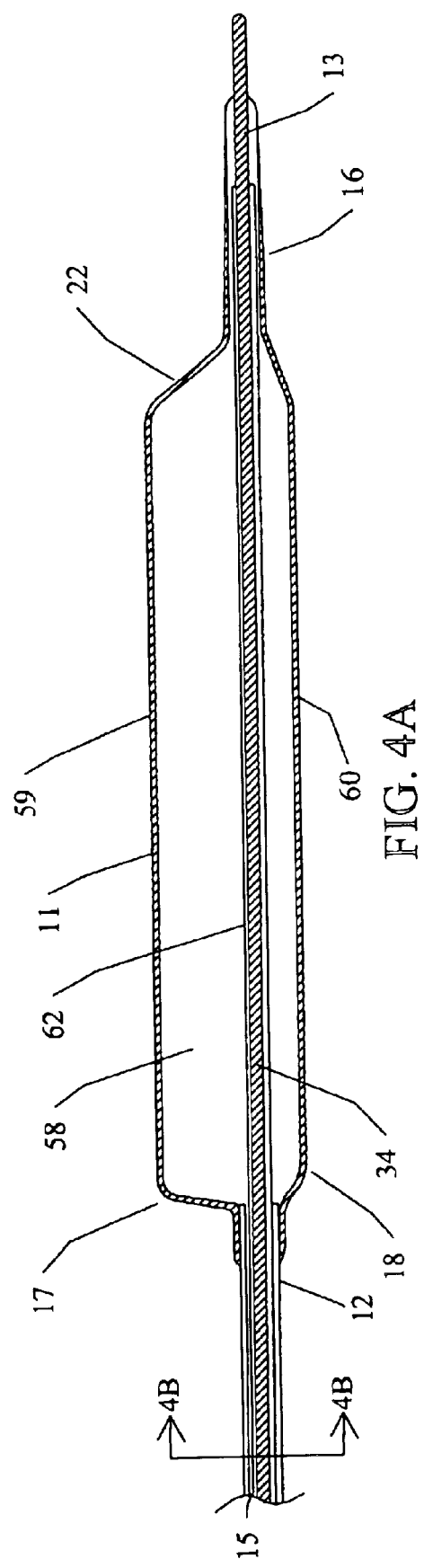
FIG. 4A depicts a cross-sectional view of an embodiment of the present invention configured for use with a standard wire guide.
Figure 4B:
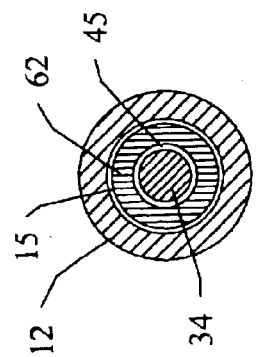
FIG. 4B is a cross-sectional view taken along line 4a—4a of FIG. 4A.

A second embodiment of the present invention is depicted in FIG. 4 that is adapted for use with a wire guide 34. The illustrative wire-guided dilation balloon 10 includes an inner sheath 62 coaxially disposed within the outer sheath 12 to which the balloon portion 11 is attached. The inner sheath 62 serves as the conduit for a wire guide 34, in one embodiment a standard 0.035" wire guide, that is loaded into, and is extendable from the inner sheath passageway 45. In the illustrative embodiment, both the inner and outer sheaths 12, 62 are made of poly-ether ether ketone (PEEK), with the outer sheath 12 having and OD of 0.85" and the inner sheath 62 having an OD of 0.50". The inner sheath 62 is sized to allow the flow of infusate through sheath passageway 15 within the annular space between the two sheaths 12, 62 and into the interior 58 of the balloon portion 11 to expand the balloon. The inner sheath 62 terminates within the distal tip portion 14 about the distal end 16 of the balloon portion or a few millimeters past. The wire guide 34 is typically utilized a support element 13 for adding stiffness or pushability to the balloon catheter 10, or it may be introduced separately into the patient. The inner sheath 62 alone may provide sufficient stiffness and pushability to function as the support element 13 for some applications, which can in some embodiments make a separate support element 13, such as a nitinol wire, unnecessary. If desired, a wire guide 34 that is most suitable as a support element 13, may at some point be replaced with a different wire guide having characteristics more desirable for a particular procedure. In the illustrative embodiment, the outer and inner sheaths 12, 62 are typically fixed relative to one another longitudinally by a standard hub (not shown), which provides access for the wire guide, and a port for the infusion of balloon infusate.

In certain embodiments, the proximal end of the balloon is indented. Such indentations can permit the endoscopist to lock or otherwise more completely engage the proximal end of the balloon with the distal end of the endoscope, thereby resisting rotational movement and thus minimizing rotational loss of balloon/scope alignment. One such exemplary embodiment comprises an indentation which effectively results in a circumferential flange at the proximal end of the balloon that is configured to frictionally engage the distal end of the endoscope.

Figure 5:
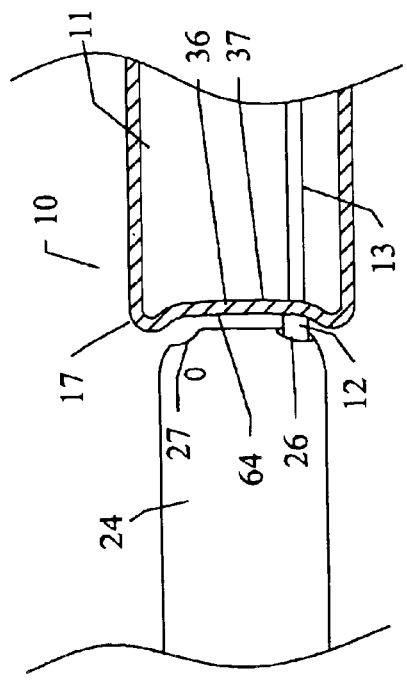
FIG. 5 depicts an embodiment of the present invention, wherein the posterior end of the balloon portion is generally concave.
Figure 6:
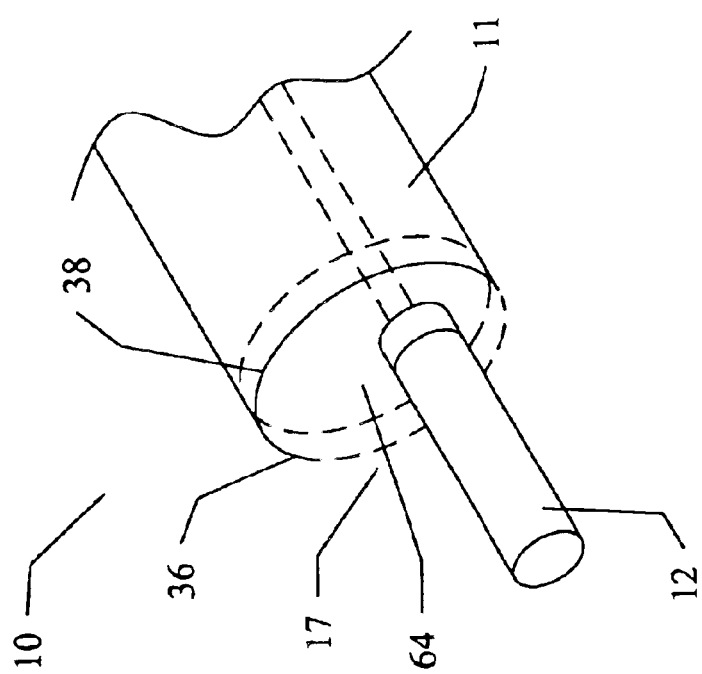
FIG. 6 depicts an embodiment of the present invention, wherein the posterior end includes a guide element to facilitate engagement with the endoscope face.

FIGS. 5–6 depicts embodiments of the balloon portion 11 that include a positive engagement guide 36 that is intended to facilitate or improve engagement and/or alignment with the face 25 of the endoscope 24. Typically, engagement results when the proximal end 17 of balloon both tightly abuts the endoscope face 25 and is correctly aligned so that central axis 21 of the balloon is generally aligned with central axis 30 of the endoscope. FIG. 5 depicts a positive engagement guide 36 that comprises a receiving area 64 comprising a concave surface 37 at the proximal end 17 of the balloon portion 11 to receive the endoscope face 25, which is typically rounded distally and therefore, naturally conforms to the concave surface 37. The concave shape of the proximal end 17 can increase the available area of the endoscope face 25 contacting the balloon portion 11, and possibly assisting with alignment as the balloon pulled back to engage the scope.

FIG. 6 depicts a balloon portion 11 that includes a guide structure 38 along the outer edge of the truncate proximal end 17 to help facilitate correct alignment and proper engagement between the scope 24 and balloon portion 11. As the balloon catheter 10 is pulled back toward the endoscope face 25, the guide structure 38 provides an additional means to help guide the endoscope against the balloon portion 11. The illustrative guide structure 38 comprises a flap-like structure that is bonded to or formed with the balloon portion 11 and that defines a receiving area 64. The guide structure 38 acts to properly seat the endoscope face 25 into the receiving area 64 at the proximal end 17 so that the balloon can be rotated and aligned accordingly. Additionally, different areas of color or other visual markers could be incorporated into the guide structure 38 to tell the endoscopist how the balloon portion 11 is oriented relative to the endoscope and whether it should be rotated. Also, the guide structure 38 may comprise merely a marker or series of markers on the surface of the balloon portion surface for indicating orientation, rather than a raised structure or structures. The flap-like guide structure 38 further serves to provide some protection against tissue or materials migrating into the space between the proximal end 17 of the balloon portion 11 and the endoscope face 25, thus limiting visibility. The illustrative guide structure 38 is merely exemplary. In view of the teachings herein, it would be within the ability of one of ordinary skill in the medical arts to conceive and design other annular or discrete structures that would accomplish the objective of providing a guide for proper engagement of the balloon portion 11 and endoscope 24.

Figure 7:
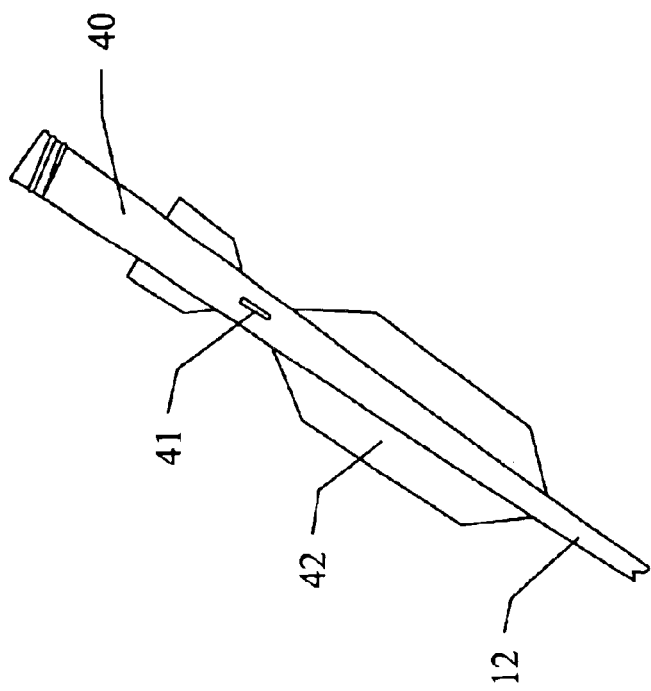
FIG. 7 depicts an embodiment of the posterior connector of the present invention which includes an alignment marker.

Another manner in which alignment can be accomplished is depicted in FIG. 7, in which an alignment marker 41 is placed on the proximal hub 40 of the balloon catheter 10 that the operator can use to tell when a particular side of the balloon is oriented upward, thereby matching the orientation of the endoscope so that they are concentrically aligned. The alignment marker can comprise any system of indicia, such as markings, characters, colors, structures, etc. that are printed on, embossed in, molded with, or otherwise affixed or attached to the hub. Optionally, the marker can be included on the strain relief element 42 or the shaft 12 itself in a location for convenient viewing during the procedure.

It should be noted that while the illustrative embodiments are generally intended for dilation of esophageal, pyloric, and colonic strictures, it is contemplated that the present invention may encompass any balloon, dilation, extraction, etc. that can be designed for endoscopic use and which may be abutted against the scope face to form a common functional unit therewith that is appropriate for a particular clinical application. These would include applications utilizing both compliant and non-compliant balloon materials.

Examples of other clinical applications include, but are not limited to, biliary tree, bronchial tree, neural endoscopy, and the vascular system.

Any other undisclosed or incidental details of the construction or composition of the various elements of the disclosed embodiment of the present invention are not believed to be critical to the achievement of the advantages of the present invention, so long as the elements possess the attributes needed for them to perform as disclosed. The selection of these and other details of construction are believed to be well within the ability of one of even rudimentary skills in this area, in view of the present disclosure. Illustrative embodiments of the present invention have been described in considerable detail for the purpose of disclosing a practical, operative structure whereby the invention may be practiced advantageously. The designs described herein are intended to be exemplary only. The novel characteristics of the invention maybe incorporated in other structural forms without departing from the spirit and scope of the invention. The inventors contemplate embodiments both comprising and consisting of the described elements. Unless otherwise indicated, all ordinary words and terms used herein shall take their customary meaning as defined in The New Shorter Oxford English Dictionary, 1993 edition. All technical terms shall take on their customary meaning as established by the appropriate technical discipline utilized by those normally skilled in that particular art area. All medical terms shall take their meaning as defined by Stedman's Medical Dictionary, 27$^{th}$ edition.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A balloon catheter for use with an endoscope comprising:
    a) a dilation balloon comprising a proximal end and a distal end, wherein said proximal end comprises a proximal opening, said proximal opening being offset from a central longitudinal axis of said balloon; and
    b) a shaft connected to said proximal opening, wherein said shaft comprises a lumen for providing an infusion pathway into said dilation balloon.

2. The balloon catheter according to claim 1, wherein said proximal end is truncated.

3. The balloon catheter according to claim 2, wherein said proximal end is indented.

4. The balloon catheter according to claim 2, wherein said proximal end is concave.

5. The balloon catheter according to claim 3, wherein said proximal end is configured to be complementary to the distal end of an endoscope, such that in use said proximal end frictionally engages the distal end of the endoscope and thereby resists rotational movement.

6. The balloon catheter according to claim 4, wherein said proximal end is configured to be complementary to the distal end of an endoscope, such that in use said proximal end frictionally engages the distal end of the endoscope and thereby resists rotational movement.

7. The balloon catheter according to claim 5, wherein said proximal end of said balloon comprises a circumferential flange.

8. The balloon catheter according to claim 6, wherein said proximal end of said balloon comprises a circumferential flange.

9. The balloon catheter according to claim 1, wherein said dilation balloon is substantially cylindrical in shape.

10. The balloon catheter according to claim 1, wherein said distal end is tapered.

11. The balloon catheter according to claim 1, wherein said distal end comprises a tip portion, wherein said tip portion is offset from said central longitudinal axis.

12. The balloon catheter according to claim 11, wherein said tip portion is flexible.

13. The balloon catheter according to claim 11, wherein said tip portion is rounded.

14. The balloon catheter according to claim 11, wherein said tip portion comprises a central bore.

15. The balloon catheter according to claim 14, wherein said central bore is filled with an adhesive.

16. The balloon catheter according to claim 11, further comprising a support element, wherein said support element is connectively disposed between said shaft and said tip portion, such that said infusion pathway is maintained between said shaft and said dilation balloon.

17. The balloon catheter according to claim 16, wherein said support element is a wire element.

18. The balloon catheter according to claim 17, wherein said wire element is nitinol wire.

19. The balloon catheter according to claim 16, where in said support element is an inner sheath, wherein said inner sheath is coaxially disposed within said shaft.

20. The balloon catheter according to claim 19, further comprising a wire guide, wherein said wire guide is extended through said inner sheath to said tip portion.

21. The balloon catheter according to claim 20, wherein said wire guide is nitinol wire.

22. The balloon catheter according to claim 1, wherein said dilation balloon is made of a transparent material.

23. A balloon catheter for use with an endoscope comprising:
    a) a dilation balloon comprising a proximal end and a distal end, wherein said proximal end is truncated comprising a proximal opening and said distal end is tapered comprising a distal opening, said proximal and distal openings being offset from a central longitudinal axis of said balloon;
    b) a shaft connected to said proximal opening, wherein said shaft comprises a lumen for providing an infusion pathway into said dilation balloon;
    c) a tip portion connected to said distal opening; and
    d) a support element, wherein said support element is connectively disposed between said shaft and said tip portion, such that said infusion pathway is maintained between said shaft and said dilation balloon,
    wherein when said dilation balloon is inflated said proximal end substantially abuts and aligns with the endoscope forming a substantially unitary cylindrical unit with the endoscope.

24. A balloon catheter for use with an endoscope comprising:
    a) an eccentric dilation balloon comprising a central axis and a luminal axis, wherein said luminal axis is offset from said central axis; and b) a shaft connected to said eccentric dilation balloon along said luminal axis.

25. The balloon catheter according to claim 23, wherein said proximal end is indented.

26. The balloon catheter according to claim 23, wherein said proximal end is concave.

27. The balloon catheter according to claim 25, wherein said proximal end is configured to be complementary to the distal end of an endoscope, such that in use said proximal end frictionally engages the distal end of the endoscope and thereby resists rotational movement.

28. The balloon catheter according to claim 26, wherein said proximal end is configured to be complementary to the distal end of an endoscope, such that in use said proximal end frictionally engages the distal end of the endoscope and thereby resists rotational movement.

29. The balloon catheter according to claim 27, wherein said proximal end of said balloon comprises a circumferential flange.

30. The balloon catheter according to claim 28, wherein said proximal end of said balloon comprises a circumferential flange.

31. The balloon catheter according to claim 23, wherein said tip portion is flexible.

32. The balloon catheter according to claim 23, wherein said tip portion is rounded.

33. The balloon catheter according to claim 23, wherein said tip portion comprises a central bore.

34. The balloon catheter according to claim 33, wherein said central bore is filled with an adhesive.

35. The balloon catheter according to claim 23, wherein said support element is a wire element.

36. The balloon catheter according to claim 35, wherein said wire element is nitinol wire.

37. The balloon catheter according to claim 23, wherein said support element is an inner sheath, wherein said inner sheath is coaxially disposed within said shaft.

38. The balloon catheter according to claim 37, further comprising a wire guide, wherein said wire guide is extended through said inner sheath to said tip portion.

39. The balloon catheter according to claim 38, wherein said wire guide is nitinol wire.

40. The balloon catheter according to claim 23, wherein said dilation balloon is made of a transparent material.

41. The balloon catheter according to claim 24, further comprising a tip portion at the distal end of said luminal axis.

42. The balloon catheter according to claim 41, wherein said tip portion is flexible.

43. The balloon catheter according to claim 41, wherein said tip portion is rounded.

44. The balloon catheter according to claim 41, wherein said tip portion comprises a central bore.

45. The balloon catheter according to claim 44, wherein said central bore is filled with an adhesive.

46. The balloon catheter according to claim 41, further comprising a support element, wherein said support element is connectively disposed between said shaft and said tip portion, such that an infusion pathway is maintained between said shaft and said dilation balloon.

47. The balloon catheter according to claim 46, wherein said support element is a wire element.

48. The balloon catheter according to claim 47, wherein said wire element is nitinol wire.

49. The balloon catheter according to claim 46, where in said support element is an inner sheath, wherein said inner sheath is coaxially disposed within said shaft.

50. The balloon catheter according to claim 49, further comprising a wire guide, wherein said wire guide is extended through said inner sheath to said tip portion.

51. The balloon catheter according to claim 50, wherein said wire guide is nitinol wire.

52. The balloon catheter according to claim 24, wherein said dilation balloon is made of a transparent material.

* * * * *